United States Patent
Hansen et al.

(10) Patent No.: US 8,888,834 B2
(45) Date of Patent: Nov. 18, 2014

(54) DEPLOYMENT ASSEMBLY AND INTRODUCER

(75) Inventors: Palle M. Hansen, Bjaeverskov (DK); Johan M. Lowinger, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 979 days.

(21) Appl. No.: 12/459,577

(22) Filed: Jul. 2, 2009

(65) Prior Publication Data

US 2010/0004606 A1 Jan. 7, 2010

Related U.S. Application Data

(60) Provisional application No. 61/133,767, filed on Jul. 2, 2008.

(51) Int. Cl.

| | |
|---|---|
| *A61F 2/06* | (2013.01) |
| *A61M 5/178* | (2006.01) |
| *A61F 2/95* | (2013.01) |
| *A61F 2/966* | (2013.01) |
| *A61B 17/00* | (2006.01) |
| *A61B 17/34* | (2006.01) |

(52) U.S. Cl.
CPC ......... *A61F 2/95* (2013.01); *A61B 2017/00371* (2013.01); *A61B 2017/00367* (2013.01); *A61B 2017/347* (2013.01); *A61F 2/966* (2013.01); *A61F 2002/9517* (2013.01)
USPC ..................... 623/1.11; 623/1.23; 604/165.01

(58) Field of Classification Search
CPC ............. A61B 2017/0057; A61B 2017/00367; A61B 20/00371; A61B 20/00389; A61B 20/00619; A61B 20/347; A61F 2/95; A61F 2002/9517
USPC .................. 600/585, 226; 604/264; 606/108; 623/1.11, 1.23
See application file for complete search history.

(56) References Cited

U.S. PATENT DOCUMENTS

| | | | |
|---|---|---|---|
| 6,402,760 B1 * | 6/2002 | Fedida | 606/108 |
| 6,599,296 B1 | 7/2003 | Gillick et al. | |
| 7,326,236 B2 * | 2/2008 | Andreas et al. | 623/1.11 |
| 7,550,001 B2 * | 6/2009 | Dorn et al. | 623/1.12 |
| 7,935,141 B2 * | 5/2011 | Randall et al. | 623/1.11 |
| 2007/0168014 A1 * | 7/2007 | Jimenez et al. | 623/1.12 |
| 2009/0024137 A1 * | 1/2009 | Chuter et al. | 606/108 |

FOREIGN PATENT DOCUMENTS

DE  198 19 634 A1  11/1999

\* cited by examiner

*Primary Examiner* — Devin Henson
(74) *Attorney, Agent, or Firm* — Brinks Gilson & Lione

(57) ABSTRACT

A deployment assembly (10) for an introducer used for introducing into a patient a stent or other device, the deployment assembly including a housing 30 carrying a sprung loaded (90) actuator (44,50). The actuator includes a toothed wheel (50) carrying a spool (48) around which a retraction strap (44) can be wound. The strap (44) is coupled to a body member (26) of the introducer and through this to the outer sheath (14) thereof. A trigger (16) is provided for operating the actuator (44, 50). When the trigger (16) is pressed, the actuator winds, under the force produced by the spring (90), the strap (44) to thereby retract the outer sheath (14) so as to expose and then deploy the device carried on the introducer. The mechanism is such that a surgeon need not expend his own energy to retract the outer sheath (14) since this force is provided by the spring (90). Furthermore, the spring (90) acts in a plane other than that of the direction of retraction of the sheath (14), which minimizes the risk of inadvertent movement of the introducer as the sheath (14) is being retracted.

29 Claims, 17 Drawing Sheets

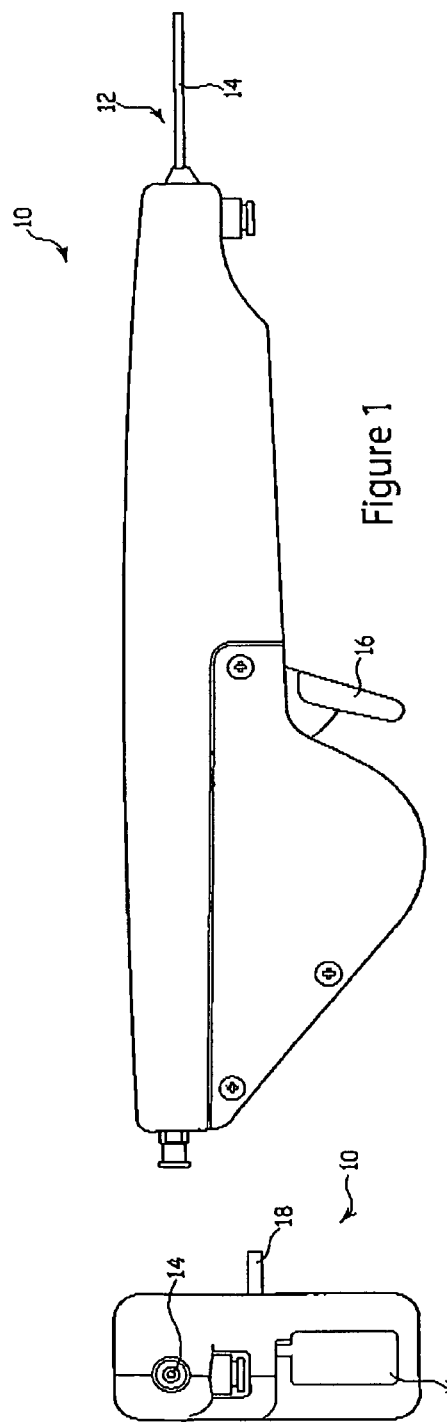

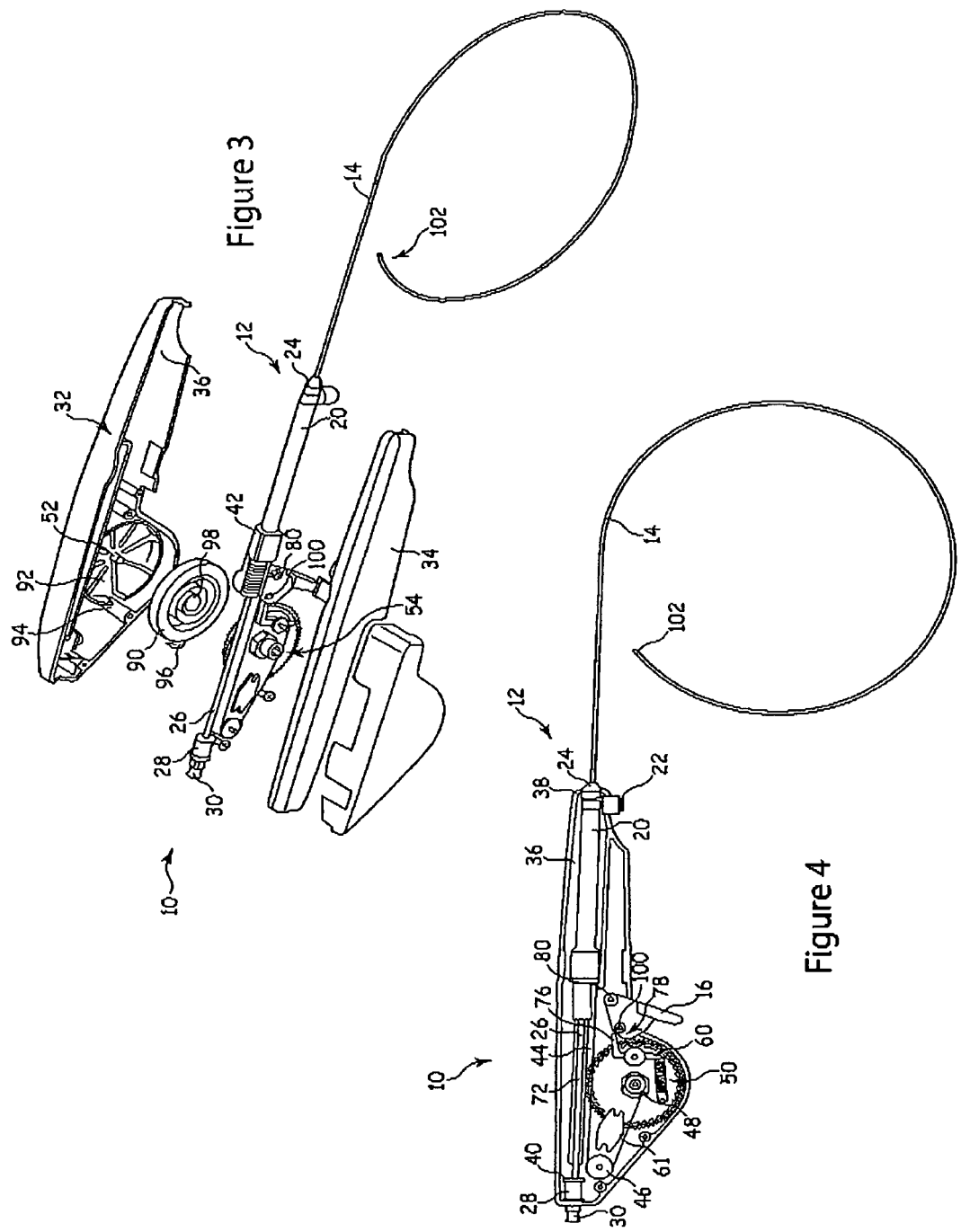

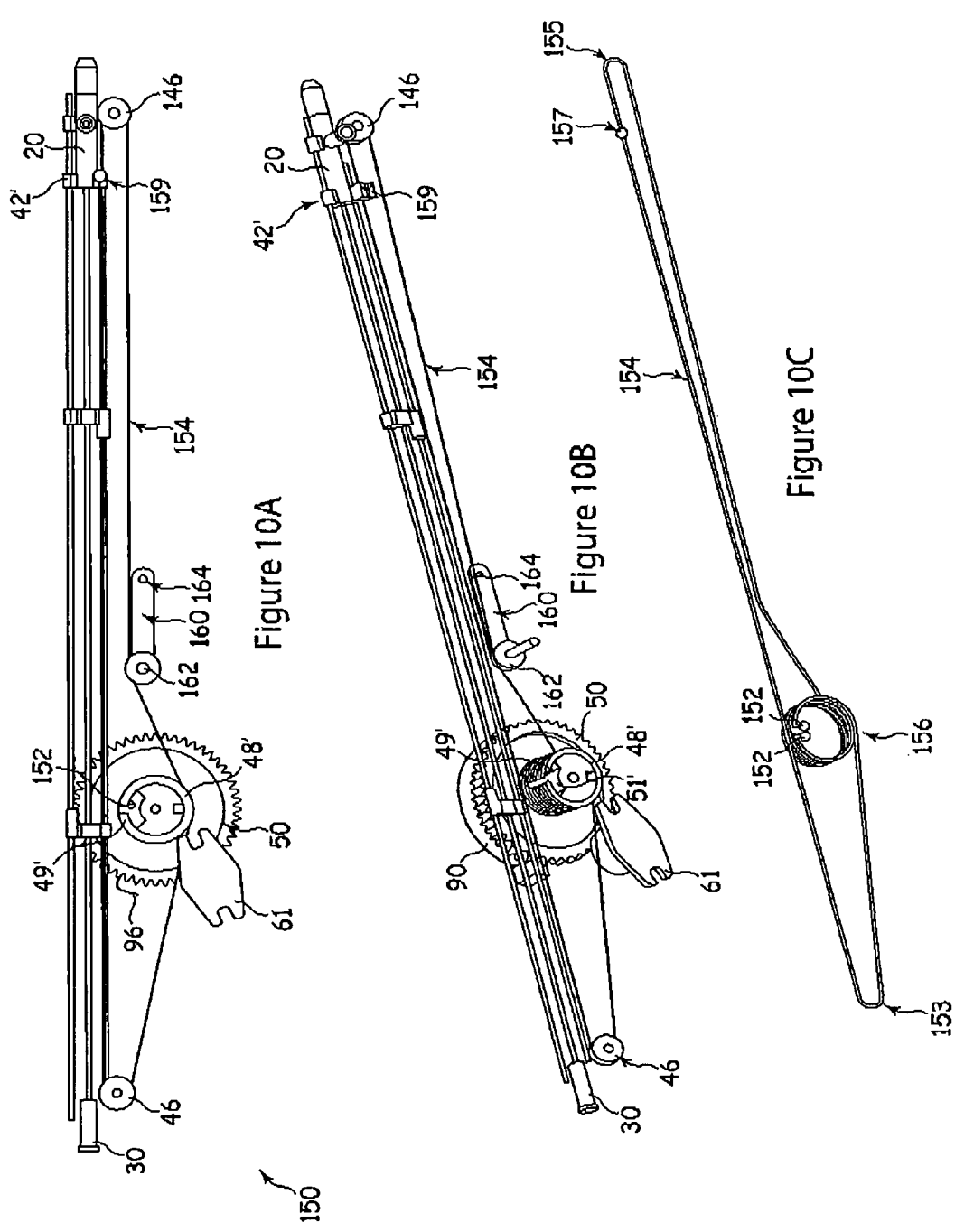

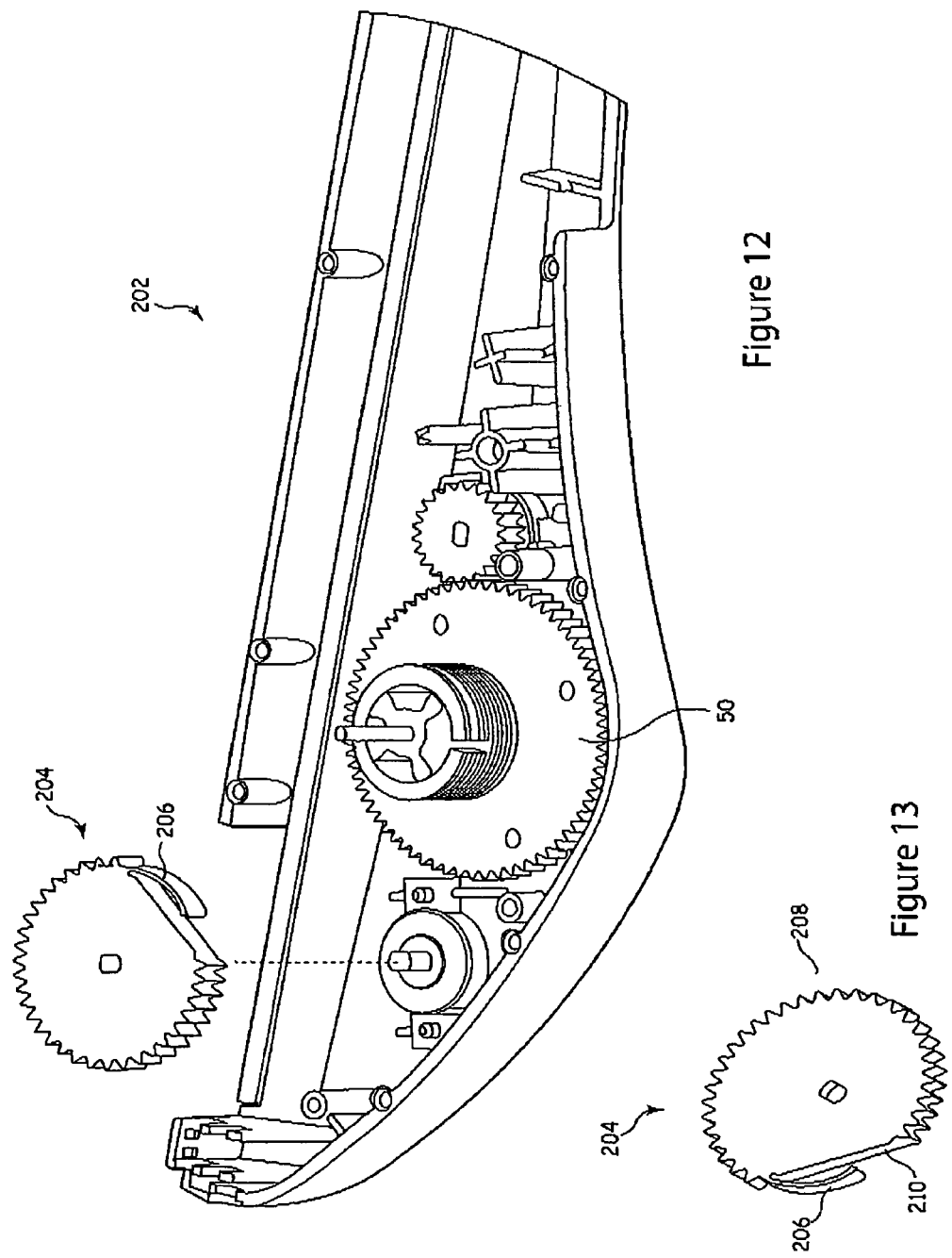

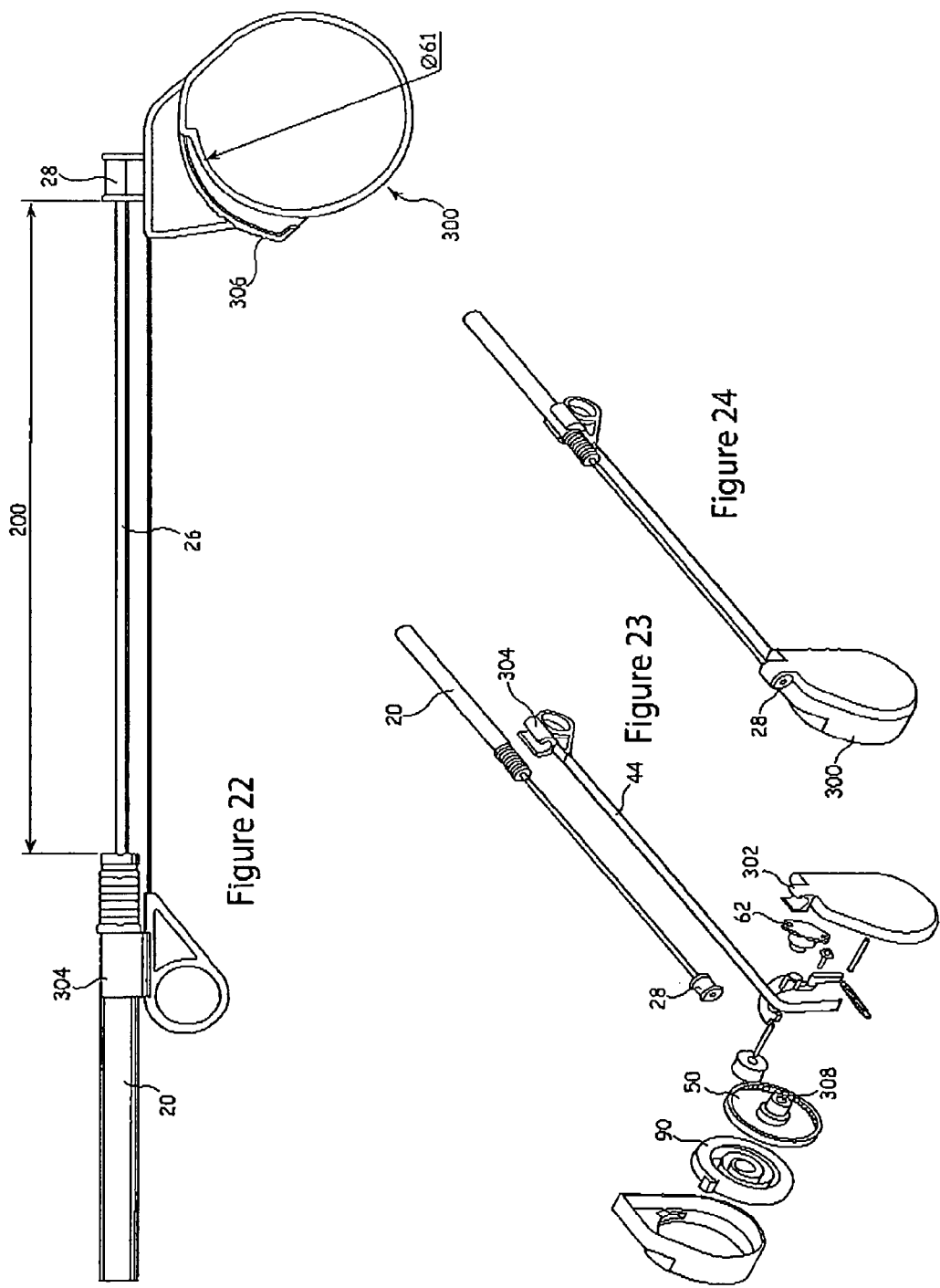

DEPLOYMENT ASSEMBLY AND INTRODUCER

CROSS-REFERENCE TO RELATED APPLICATIONS

This application claims priority of provisional application Ser. No. 61/133,767, filed Jul. 2, 2008.

TECHNICAL FIELD

The present invention relates to a deployment assembly for deploying one or more components of an endovascular introducer assembly, as well as to an introducer assembly and the components thereof.

BACKGROUND OF THE INVENTION

The art of endoluminal prosthesis is well developed, being used for the deployment of implants, prosthesis and other medical devices, as well as for administering drugs and diagnostic purposes.

In particular in connection with the deployment of implants, prostheses and other medical devices, such introducers are typically provided with an outer sheath within which the device to be introduced and other necessary medical equipment is fed. In the case of a device being introduced into a patient, this is generally pre-loaded onto the introducer within the sheath. The sheath is then introduced endoluminally using, for example, the well known Seldinger technique. When the distal end of the introducer is positioned in the correct location, i.e., at the treatment site, the device to be deployed is released from the introducer into the patient. Deployment typically involves retracting the outer sheath so as to expose the device and then expanding or allowing the device to self-expand.

Current systems generally require the physician to withdraw the outer sheath by applying a manual force to a component of the outer sheath at a location near the proximal end of the introducer, which remains outside of the patient during the procedure. Typically, this is achieved by the physician pulling the outer sheath in a proximal direction whilst holding steady the components of the introducer upon which the device to be deployed is held. This generally involves a two-handed operation by the clinician and risks movement of the introducer during the deployment process such that the device fails to be deployed at the correct location within the patient. This risk is particularly acute in situations where it is required to apply a reasonably substantial force to retract the outer sheath to expose the device to be deployed, such as with larger introducer systems and introducers made to follow a tortuous path within the patient.

Attempts have been made to address the difficulties of such introducer systems and reference is made, for example, to the following patent publications: US Patent Publication No. 2005/0090887, U.S. Pat. No. 6,206,888, US Patent Publication No. 2006/0286145, U.S. Pat. No. 6,113,608, and WO 2004/014256.

The devices disclosed in the above references seek to address a part of the difficulties encountered with introducers of this nature but provide either relatively complex systems or systems which do not address the entirety of the problems. A difficulty with such systems is that it is important not to cause a physician to lose control of the deployment process. Moreover, some of the above-disclosed systems are suitable only for one specific device. However, since deployable devices vary in their nature as a result of the device itself as well as of the condition/nature of the patient, these systems would necessitate either the production of different deployment systems for different types and sizes of devices and/or particular medical procedures, or for the use of systems which are not entirely adapted to the particular medical condition of the patient sought to be treated.

SUMMARY OF THE INVENTION

The present invention seeks to provide an improved introducer system and an improved deployment assembly for such a system. According to an aspect of the present invention, there is provided a deployment assembly for deploying one or more components of an endovascular introducer assembly provided with a retractable element, the deployment assembly including an external manipulation element, and a sprung-loaded actuator element coupled to the external manipulation element, wherein at least part of the restoring force exerted by the sprung loaded element is at an angle to a direction of retraction of said retractable element along said external manipulation element.

The feature of the actuator being able to provide at least a part of its restoring force in a direction other than the direction of retraction of the retractable element can provide a smaller and in some instances substantially no force component in the withdrawal direction of the introducer. As a result of this, there can be significantly less jolting of the introducer in the longitudinal direction thereof and thus less risk of the distal end of the introducer being moved unintentionally out of position. This problem can manifest itself with systems which may provide a large force in the withdrawal direction.

In the preferred embodiment the sprung loaded actuator element includes a spiral spring, which in practice has virtually no resultant restorative force in any particular direction but substantially solely a rotational restorative force. Another example provides a compression spring which is oriented at an angle to the retraction direction, for example at 30°, 45° and even up to 90°.

The spring may be kept in extension tension or it may be kept in compressive tension, the latter providing a pushing action to push the outer sheath backwards, rather than pulling this as would be the case with a spring which is stretched in tension.

The advantage of the above features is that when the spring is released so as to retract the sprung element to thereby withdraw the sheath, the force produced by the spring is less likely and in most instances unlikely to cause the introducer to jolt in the retraction direction.

As explained above, such jolting can unintentionally move the distal end of the introducer and thus cause a device carried on the introducer to move from the desired position right at the time of deployment.

Advantageously, the deployment assembly includes a speed control device.

According to another aspect of the present invention, there is provided a deployment assembly for deploying one or more components of an endovascular introducer assembly provided with a retractable element, the deployment assembly including a sprung-loaded actuator element, a coupling element for coupling the deployment device to a said retractable element and a speed control device for controlling the speed of operation of the actuator element.

The provision of a speed control element to control the actuator and thus the retraction of the retractable element can ensure that the retraction process is effected smoothly as well in an automated manner, thus avoiding the need for a clinician to expend manual force in the process. As a result, the entire retraction process can be effected smoothly and efficiently. Additionally, the provision of a controllable automated retraction system of this nature can free up one of the clinician's hands, thereby leaving this available for other control operations, such as guiding the introducer or any other necessary or desired action.

In all of the above aspects of the present invention, it is preferred that the speed control device provide for adjustable speed of retraction.

Advantageously, the speed control device is separately actuatable relative to the actuator element. It may be a part of the actuator element and/or the trigger thereof.

Preferably, the assembly includes a trigger device for triggering the actuator element to retract a retractable element attached thereto. The trigger element may include a stop device operable to stop operation of the actuator.

In the preferred embodiment, the sprung actuator element includes a spiral spring. This has the advantage of being able to have a strong spring providing a long withdrawal motion yet in a compact arrangement and one which does not produce excessive forces on the casing of the introducer. In fact, the spiral spring can produce virtually no resultant movement force on the handle assembly of the introducer.

The coupling element preferably includes an elongate flexible member attachable to a said retractable element to couple said retractable element to the sprung actuator element. The flexible member may be a cord, strip or band of flexible material.

Advantageously, the speed control element is operable to control a frictional force applied to the elongate flexible member. In an embodiment, the speed control element includes an adjustable labyrinthine path for the elongate flexible member.

BRIEF DESCRIPTION OF THE DRAWINGS

Embodiments of the present invention described below, by way of example only, with reference to accompanying drawings, in which:

FIG. 1 is a side elevational view of an embodiment of deployment assembly of FIG. 1;

FIG. 2 is a front elevational view of the embodiment of deployment assembly;

FIG. 3 is an exploded view of the assembly of FIG. 1 showing the components thereof;

FIG. 4 is a side elevational view of the introducer of FIG. 1 having cover parts thereof removed;

FIG. 10*a* is a side elevational view of some of the internal components of another embodiment of handle assembly;

FIG. 10*b* is a perspective view of the embodiment of FIG. 10*a*;

FIG. 10*c* is a perspective view of a draw cable of the embodiment of FIGS. 10*a* and 10*b*;

FIGS. 12 to 18 are perspective views of another embodiment of handle assembly at different times during assembly;

FIG. 22 is a side elevational view of another embodiment of deployment device;

FIG. 23 is a perspective view of the device of FIG. 19 in exploded form;

FIG. 24 is a perspective view of the device of FIGS. 19 and 20 in assembled form.

DETAILED DESCRIPTION

Figure 5:
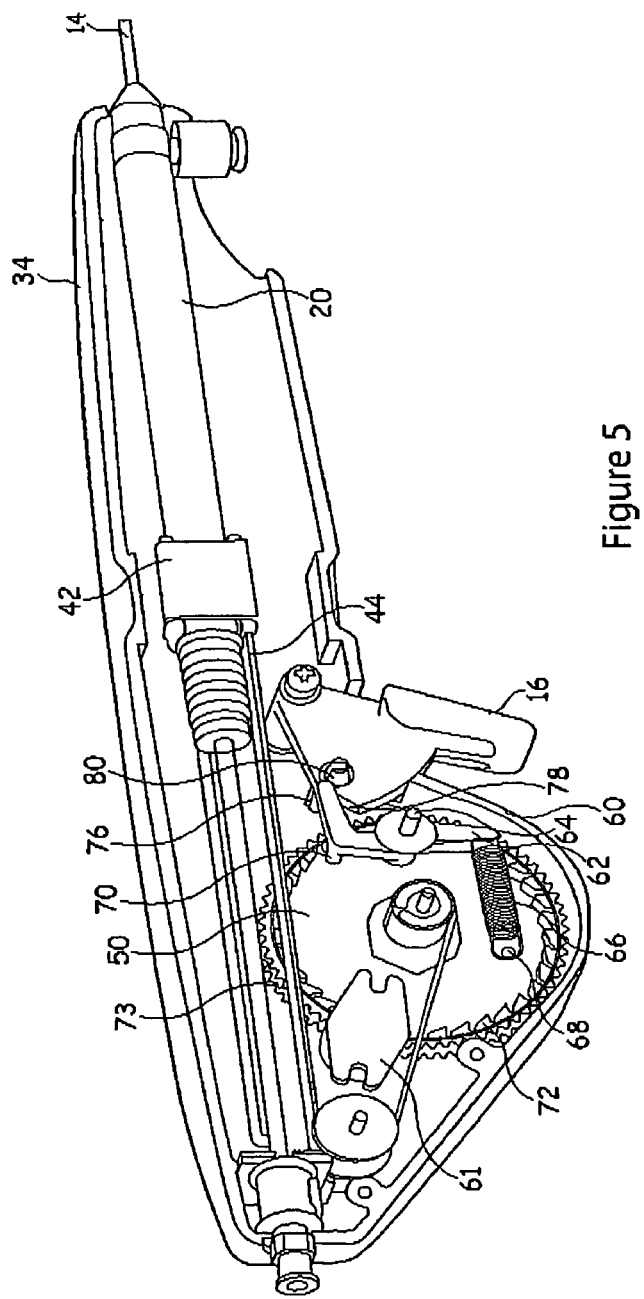
FIG. 5 is a schematic perspective view showing in better detail some of the components of the assembly of FIG. 1.

Referring to FIG. 1, there is shown a handle 10 for an introducer 12. This particular embodiment is designed to accommodate the applicant's Zilver™ stent introducer available from the applicant. As is described in more detail below, the handle 10 of this embodiment is designed to fit over the conventional handle of a Zilver™ introducer and operate the Zilver™ introducer in a manner analogous to similar introducers provided with a catheter assembly 14 having an outer sheath which houses an inner catheter and, in this particular example, a Zilver™ stent disposed on the inner catheter for deployment into the lumen of a patent.

The handle 10 is provided with a trigger 16 which can be pressed by a clinician, in a manner analogous to a gun trigger, in order to operate the handle 10 to deploy the stent.

Referring to FIG. 2, the handle 10 is shown in front elevational view, where it can be seen that there is provided a locking pin 18 on one side of the body of the handle 10 and which in use acts to lock the trigger 16 such that it cannot be actuated until release of the locking pin 18. Locking pins of this nature are known in the art and a number of possibilities for the locking pin 18 are described below.

The handle of FIGS. 1 and 2 is designed in terms of shape and size to fit easily within the hand of a clinician. It is envisaged that for this particular embodiment, the handle could have a length of between 25 to 30 cm, a width of between 3 to 4 cm and a depth from the top of the handle portion to the hand grip below the trigger of between 7 to 8 cm.

The handle 10 is designed to provide automatic retraction of the sheath 14 upon depression of the trigger 16, such that the clinician need not expend any manual retraction effort of the type required in conventional introducer systems. This is particularly achieved by the provision of a sprung loaded actuator mechanism provided within the handle 10 and described in further detail in connection with FIGS. 3 to 9.

Referring now to FIGS. 3 and 4, there is shown the handle 10 of FIGS. 1 and 2 in the exploded form in FIG. 3 and with one part of the housing of the handle 10 removed in FIG. 4, to thereby show the internal components thereof in their assembled positions.

In these Figures, the Zilver™ introducer currently available can also be clearly seen. This includes a body element 20 which houses one or more haemostatic seals of known form and which includes a side arm 22 provided with a flushing port (not shown in FIGS. 3 and 4). The outer sheath 14 is fixed to the body 20, in this particular embodiment by a screw fitting 24.

The introducer also includes a metal cannula 26 which is coupled to an inner catheter (not shown) housed within the outer sheath 14 and on which a stent is located for deployment. At a proximal end of the cannula 26 there is provided a hub 28, which is conventionally used by a physician as a finger support for use in withdrawing the stent from the introducer.

The hub 28 is provided with an inner support stylet 30 at its proximal end. The stylet has a bore/lumen therein aligned with the bore/lumen in the metal cannula for the feeding of a guide wire through the introducer 12.

The metal cannula 26 is typically provided with a radial groove (not shown) at a distal end thereof which aligns with an aperture in the body 20 and into which a locking pin can pass. The arrangement is such that the locking pin is provided with two locking fingers which engage into the groove in the metal cannula through the slot in the body 20 to thereby lock the metal cannula to the body 20 and thus the hub 28 in the extended position shown in FIGS. 3 and 4, until the locking pin is removed. This arrangement is well known in the art and can, in some embodiments of actuator handle, take the form of the locking pin 18 of FIG. 2. In other embodiments described below, the locking pin 18 cooperates with the trigger 16.

In practice, as with most existing introducers, the device carried by the introducer is conventionally deployed by the physician holding the two parts of the deployment assembly, in this particular case the hub 28 and the body 20, and then applying a physical force in the direction of withdrawal by pulling the body 20 towards the hub 28 while simultaneously holding the hub 28 steady, thereby pulling the sheath 14 in a proximal direction relative to the hub 28. This action can make it difficult to hold the distal end of the introducer steady during deployment of the device and thus ensure that the device is maintained in the correct position during its deployment. These problems can be exacerbated by the fact that the first part of the retraction operation tends to require a greater starting force of retraction in light of the greater friction between the outer sheath 14, the inner catheter, and the device to be deployed. This tends to result in a jerky initial movement during deployment. Furthermore, in the case of a stent in particular, once the outer sheath 14 has begun to move, the retraction force becomes progressively less, tending to result in an increased speed of retraction of the outer sheath 14 and subsequent loss of precise control of the deployment process. In addition, there is a tendency for the proximal end of the stent (i.e., the end furthest from the distal tip of the introducer and typically the downstream end of the stent in the direction of blood flow) to spring out of the introducer if the sheath is not carefully and gently retracted towards the end of its span of operation.

As can be seen in FIGS. 3 and 4, the handle 10 is formed of two primary housing portions 32, 34, and includes an internal space or chamber 36 which is sized and shaped to accommodate the body portion 20 of the Zilver™ introducer as well as the cannula 26 and hub 28. Typically, there are provided a number of holding elements 38, 40, such as walls, buttresses or other protrusions, for holding these components and/or providing strength or rigidity to the handle 10. Such holding elements are well within the ability of the skilled person to devise and are therefore not described in detail herein.

A clip 42 attaches to the proximal end of the body portion 20 of the introducer and is itself coupled to or integral with a flexible actuator ribbon or strap 44 used in pulling the introducer body element 20 backwardly, as explained in detail below. Within the housing of the handle assembly 10 there is also provided a pulley wheel 46 around which the ribbon 44 passes towards a wind-up reel or spool 48 around which the ribbon 44 can be wound. Two of a variety of possible locations for the pulley wheel 46 are shown in FIGS. 3, 4 and 5. Of course, the exact location of the pulley wheel 46 is not critical as this is intended simply to provide a distance by which the sheath can be pulled back sufficiently to uncover the device held therein. Thus, the pulley wheel 46 can be positioned at any location which provides a spacing from the clip 42 that is equivalent to at least the required retraction distance.

Figure 6:
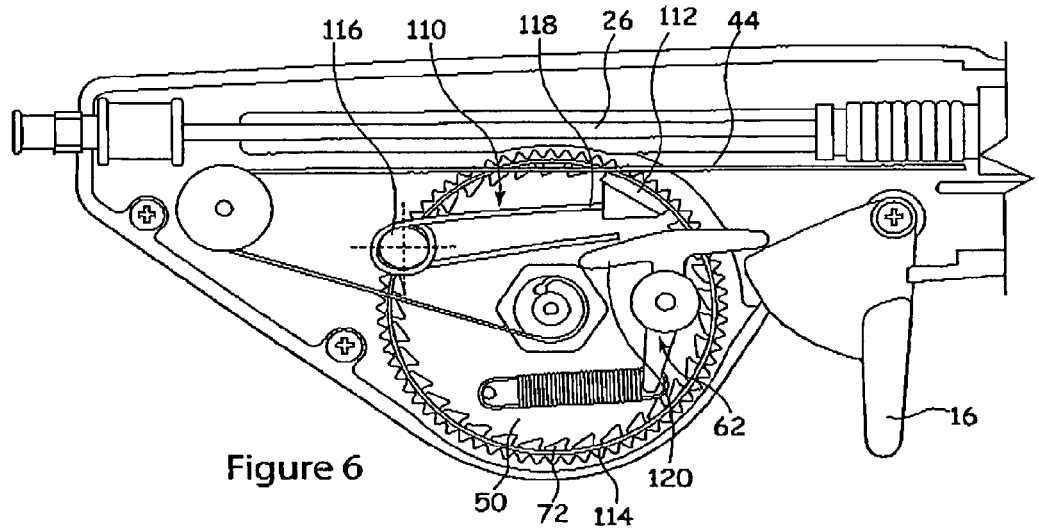
FIG. 6 is an enlarged side elevational view of the assembly of FIG. 1 with a cover element thereof removed to show in better detail a speed control element of the device.

As best seen in FIG. 6, the free end 45 of the strap 44 is held within a slot 47 in the wind-up spool 48 of the toothed wheel 50. The free end 45 may have an enlarged thickness for holding purposes.

The wind-up spool 48 is provided integrally with a toothed wheel 50 that is rotatably located in the housing of the handle 10 on one or more bosses 52. In the particular example shown, the boss 52 cooperates with a pin 54 fitted to the toothed wheel 50 and the wind-up reel 48.

The toothed wheel 50 has two primary components with which it cooperates, the first being a lock element 60, which in turn cooperates with the trigger 16. The second is a damper device 61, which is described in further detail below.

The locking element 60 can be seen in particular in FIGS. 3, 4 and 5. It includes a pivotable arm 62 which is carried on a pivot spindle 64 and is biased to a locking position by a coil spring 66. The coil spring is held at a first end to the locking arm 62 and at a second end to a suitable boss 68 conveniently formed within the casing half 34 of the handle 10. The spring 66 is such that it is normally in a stretched condition and thus biases the end 60 of the locking arm 62 in a contracting direction of the spring 66. This causes the opposite end 70 of the locking arm 62 to come into engagement with the toothed wheel 50.

As can be seen in FIG. 4, the toothed wheel 50 is provided with a set of internal teeth 72, as well as a set of external teeth 73 (the latter being more clearly visible in FIG. 5). The internal teeth 72 cooperate with a stop shoulder (not shown) located on the side of the end 70 of the locking arm 62 that is opposite of the side that is visible in the drawings, in what could best be described as a ratchet and pawl arrangement. A suitable design for such a stop shoulder will be evident to the skilled person and is thus not described in further detail herein.

Thus, when the trigger 16 is not actuated, the spring 66 biases the locking arm 60 clockwise, in the view of FIGS. 3 to 5, to thereby cause the stop shoulder to engage with the internal teeth 72 of the toothed wheel 50, thereby locking the toothed wheel 50 such that it cannot rotate to wind the ribbon 44 onto the spool 48 and retract the sheath 14.

The locking end 70 of the arm 62 is provided with a front extending foot 76 which extends beyond the perimeter of the toothed wheel 50 and which in use, as can be seen in particular in FIGS. 4 and 5, comes into contact with a sloping surface 78 of the trigger 16.

The trigger 16 is itself pivoted about a pivot point 80, such that when the trigger 16 is pulled inwardly (that is, to the left in the views of FIGS. 3 and 4), in the same manner as a gun or electric drill trigger is pulled, the surface 78 pushes the extending foot 76 upwardly, which causes the locking element 60 to rotate anti-clockwise to move the stop shoulder out of engagement with the internal teeth of the toothed wheel 50. The toothed wheel 50 thus becomes free to rotate.

The damper 61 can be any suitable damper which has a tooth gear wheel able to cooperate with the radially outwardly extending teeth 73 of the toothed wheel 50. It may, for example, be a rotary damper of the type available from Ace Controls, Inc. of 23435 Industrial Park Drive, Farmington, Mich. 48335-0071, USA. Such a damper ensures smooth rotation of the toothed wheel 50 and will prevent it from rotating beyond a predetermined speed of rotation, as will be apparent to a person skilled in the art.

The basic embodiment of the device shown in FIGS. 3, 4 and 5 includes, in addition to the components described above, a spiral spring 90, which fits within a recess 92 of the handle half 32. The outer end 96 of the spiral spring in curved backwardly and engages a shoulder 94 of a wall forming the recess 92, such that the end 96 of the spring 90 is normally held in a fixed position. The inner end 98 of the spring 90 is bent at an angle and disposed within a slot in a protrusion or boss (neither shown) on the reverse side of the toothed wheel 50, such that the inner end 98 is fixed relative to the toothed wheel 50.

The spiral spring 90 is assembled in the housing 92 in a wound-up condition. The resulting tension in the spring 90 imparts on the toothed wheel 50, in the views shown in FIGS. 4 and 5 in particular, a rotation force in an anti-clockwise direction. The locking arm 62 prevents the toothed wheel 50 from rotating until the trigger 16 is depressed by the operator. More specifically, when the trigger 16 is depressed in order to move the locking arm 62 out of reach of the internally disposed teeth 72 of the toothed wheel 50, the toothed wheel 50 becomes unlocked and can then rotate under the unwinding force of the spring 90. As the toothed wheel 50 rotates in an anti-clockwise direction, the strap 44 is progressively wound around the spool 48. The winding of the strap 44 causes retraction of the clip 42 and thus retraction of the sheath 14.

A spiral spring is preferred for this application as it provides a substantially constant return force over its range of movement as compared to many other types of springs such as coil springs, leaf springs and the like. As a result, a spiral spring can provide a reasonably constant retraction force on the sheath 14. In addition, a spiral spring can provide a greater "pull" distance (retraction span) over which the spring can provide a force that is sufficient to pull back the sheath 14.

As described above in connection with FIG. 2, the safety locking key 18 ensures that the handle of the trigger 16 cannot be actuated inadvertently, for example during packaging, shipping or transport, to cause premature deployment of the introducer. In one particular embodiment, as can be seen in FIGS. 3 and 4, the safety key 18 includes an end 100 which fits within a suitable aperture within the trigger 16 and is also held in an aperture of the casing 32. While the end 100 is positioned as shown in the figures, the trigger 16 is prevented from being moved. The trigger 16 can only be moved once the safety key 18 has been removed.

In use, the initial deployment stages of the introducer are analogous to existing methods. That is, the distal end 102 of the introducer is inserted percutaneously into a patient and fed through the patient's vasculature to the site at which the device (a stent in this example) is to be deployed. Once in this position, and once the safety key 18 has been removed, the surgeon can initiate the deployment of the device by pressing the trigger 16, and can thereafter control or regulate the deployment procedure by suitable control of the trigger 16.

More specifically, upon pressing the trigger 16 inwardly, the locking device 62 is moved to an unlocked position, thereby allowing the spring 90 to unwind, which in turn causes the toothed wheel 50 to rotate anticlockwise and the strap 44 to wind onto the spool 48. The body member 20 and thus the sheath 14 are retracted by this action, which occurs steadily under the damping effect of the damper element 61.

Should at any stage the surgeon wish to halt the retraction of the sheath, he can release the trigger 16, whereupon the spring 66 pulls the lower end 60 of the arm 62 in its contraction direction, thereby causing arm 62 to rotate clockwise until the stop shoulder of the end 70 element comes into engagement with the internal teeth 72 of the toothed wheel 50. This brings the rotation of the toothed wheel 50 to a halt and thus stops further retraction of the outer sheath 14. Retraction of the sheath can be resumed by once again pressing on the trigger 16.

At the start of the deployment procedure the spring 90 is in its most tense state and thus produces the greatest unwinding force. This is particularly advantageous because, as explained above, the first stage of retraction tends to be the hardest as a result of increased friction between the device carried on the introducer and the other elements of the introducer assembly. As the spring 90 unwinds, the force it generates reduces but so does the force necessary to continue retracting the sheath 14. Thus, there is some correspondence between the reduced force required to withdraw the sheath 14 during the deployment process and a reduced force produced by the spring 90 as it unwinds.

It will be appreciated that this system provides a very simple yet very effective mechanism for deploying a device carried at the distal end of the introducer. The requirement for a clinician to expend the force to pull back the sheath 14 is eliminated by the provision of the spring 90. Thus, the surgeon can concentrate upon the correct placement of the distal end of the introducer and upon the deployment of the device carried thereon rather than having to concentrate upon the effort to move the various components of the assembly. Furthermore, he need not use both hands to pull back the sheath, as is necessary in prior art systems, thus freeing one hand to guide the introducer as the device is being deployed. In addition to this, the system avoids, by the specific construction of the disclosed embodiments, producing a sheath retraction force which is in the longitudinal direction of the introducer. In prior art systems which require or which provide a pulling force in the longitudinal direction of the introducer, there is the risk that this force will cause the distal end of the introducer to move within the patient and thus for the device to be deployed in an incorrect location within the patient. By contrast, providing a spring which moves in a direction/or in a plane which is different from the longitudinal direction of the introducer, the risk of any such movement caused by the forces generated during retraction is minimized. In the particular embodiment described above, the force is a rotary force which provides no particular component in the longitudinal direction of the introducer and is therefore especially beneficial.

The specific embodiment shown in the Figures provides an additional advantage for the subsequent steps of deployment of the device carried out by the introducer. Namely, as the strap 44 winds onto the spool 48, the effective diameter of the spool increases. Thus, for every additional rotation of the toothed wheel 50, the effective circumference of the spool 48 increases, thereby taking up more length of strap 44 during each rotation and thus speeding up the rate of retraction of the outer sheath 14. This has the effect of increasing the speed at which the device is released from the introducer during the deployment procedure, which can be advantageous in some instances, such as when it is desired to restore full blood flow as quickly as possible.

Figures 7A, 7B:
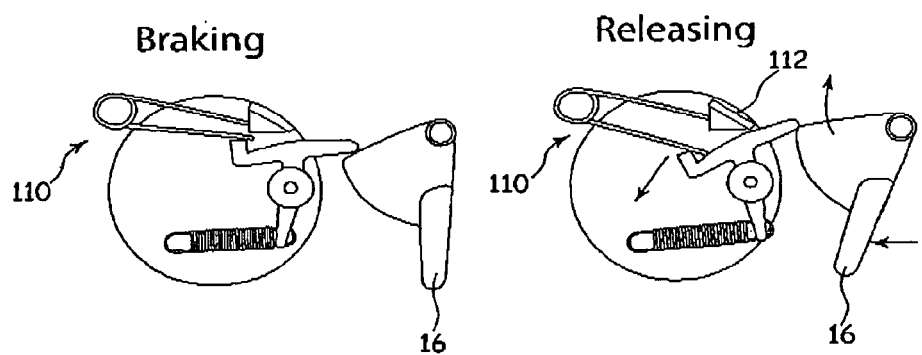
FIGS. 7*a* and 7*b* are schematic views showing the assembly of FIG. 1 in a braking condition and in a releasing condition, respectively.

The embodiment shown in FIGS. 3 to 5 provides a substantially even deployment speed, as determined by the damper 61. However, it is contemplated that in some instances the clinician would wish to have additional control of the speed of retraction of the outer sheath 14, and for this purpose additional embodiments are shown in FIGS. 6 to 7B and 8 to 9B. Referring first to FIGS. 6 to 7B, there is shown an embodiment which includes a brush or breaking mechanism 110 comprising a brush head 112 which is arranged to brush against an interior surface of a wall 114 of the toothed wheel 50. The brush head 122 could equally be made to engage or brush along with the internal teeth 72 in some embodiments.

The brush head 112 is attached to a spring element 114 held on a pin 116 projecting from an internal surface of the casing (typically of the half 34 of the casing). The other end 118 of the spring 110 rests on an enlarged head 120 of the locking arm 62. As will be apparent from FIGS. 7A and 7B, as the trigger 16 is depressed, the enlarged head 20 pivots in a counter-clockwise direction, thereby opening up the spring element 110. This allows it to expand such that the pressure brought by the spring 110 on the brush head 112 reduces the more the trigger 16 is depressed. This reduces the friction force applied by the brush head 112 against the internal wall 114 of the toothed wheel 50 to thereby allow the toothed wheel 52 to rotate faster under the force of the spiral spring 90. In other words, the brush head 112 acts in a manner not dissimilar from that of a conventional brake of a bicycle.

With the above described mechanism, the clinician can control the speed of rotation of the toothed wheel 50 and thus the speed of retraction of the outer sheath 14. This control is in addition to the ability to halt retraction completely by releasing the trigger 16, which as explained above causes the locking arm 62 to re-engage the internal teeth 72 of the tooth wheel 50.

Although the embodiment of FIGS. 6 to 7B does not show a damper 62 of the type shown with respect to the embodiment of FIGS. 3 to 5, such a damper could be included if desired.

Figure 8:
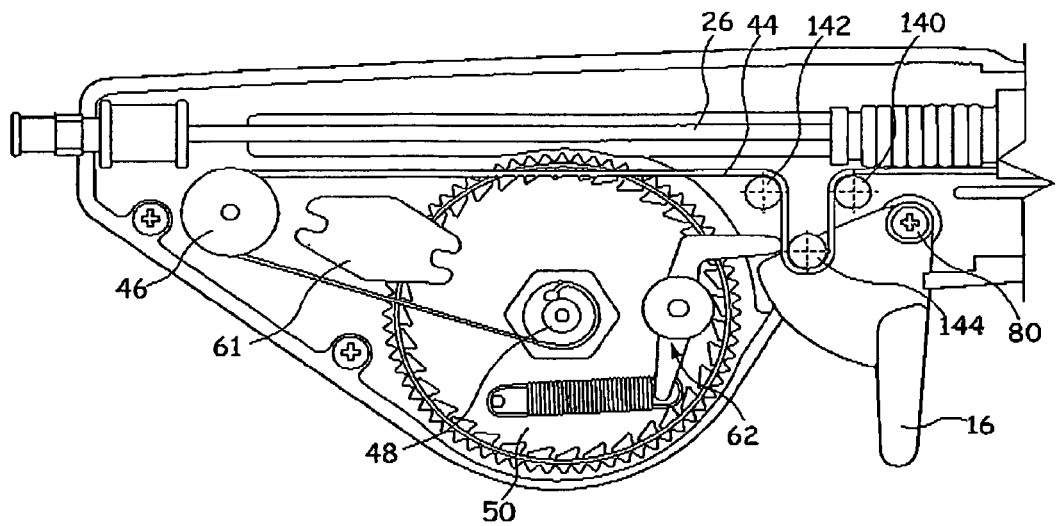
FIG. 8 is a side elevational view of the assembly of FIG. 1 with a cover element thereof removed and showing an embodiment of speed control device.
Figures 9A, 9B:
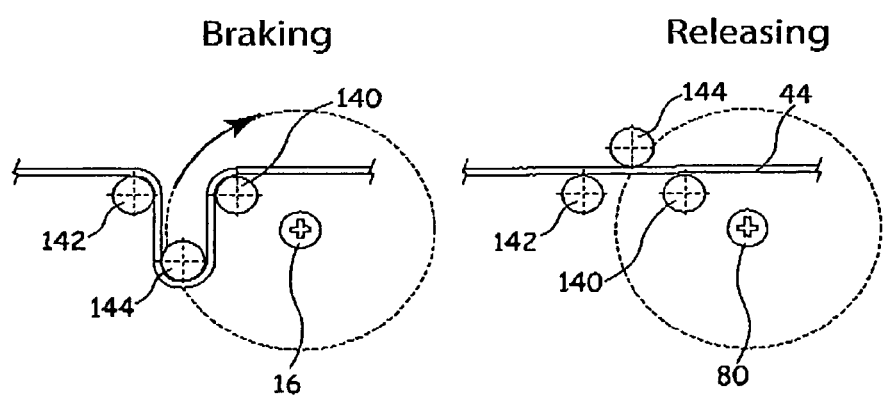
FIGS. 9*a* and 9*b* are schematic views of the locking device of FIG. 8 in a braking condition and in a releasing condition, respectively.

Another embodiment incorporating a speed control mechanism shown in FIGS. 8 to 9B. The casing 32 of the handle is shown being provided with two bosses 140, 142 which are arranged in alignment with one another in the direction of the strap 44. The trigger 16 is also provided with its own boss 144. The strap 44, attached to the outer sheath 14 and wound on to the spool 48, wraps around the bosses 140, 142, 144 in the manner shown in FIG. 8. When the trigger handle 16 is in its released condition, the boss 144 is disposed underneath the bosses 140, 142, thereby causing the strap 44 to pass down and then back up again in a U-shape around the bosses 140, 142, 144, as shown in particular in FIGS. 8 and 9A.

When the trigger 16 is pressed so as to move to the left of FIG. 8, the boss 144 pivots upwardly following a path similar to that of the dotted circle shown in FIGS. 8 to 9B. In the trigger's most depressed condition shown in FIG. 9B, the boss 144 is disposed above the plane of the bosses 140, 142, allowing the strap 44 to be fully straight and thus not to be affected by the additional friction otherwise provided through the tortuous path of the bosses 140, 142, 144. In its lowermost position, shown in FIGS. 8 and 9A, it is desirable that as much friction as possible is imparted to the strap 44 in order to provide a substantial braking or friction force. In some embodiments, this force might be enough to arrest the movement of the strap 44 completely, although in other embodiments (such as the configuration of FIGS. 8 and 9A) there might still be slippage of the strap 44 once the locking arm 60 has been disengaged.

As the trigger 16 is pressed gradually inwardly, the friction imparted to the strap 44 is gradually reduced, thereby allowing the toothed wheel 50 to rotate progressively faster under the action of the spiral spring 90, thereby controlling the speed of retraction of the sheath 14. When the trigger 16 is fully depressed, it is preferred that the bosses 140-144 provide minimal resistance to movement of the strap 44 and thus minimum resistance to the retraction force provided by the spring 90.

In some embodiments one or more of the bosses 140-144 may be provided with a friction enhancing surface, such as a roughened or grooved surface, or may comprise a material having a relatively high coefficient of friction.

The embodiments of FIGS. 6 to 7B and 8 to 9B thus provide various mechanisms for controlling the speed of retraction of the sheath 14, giving the surgeon yet further control over the deployment process.

Although the embodiments of FIGS. 6 to 9B do not show provision for the safety key 18, it will be apparent to the person skilled in the art this could be included in any of the embodiments of these Figures.

Figure 11:
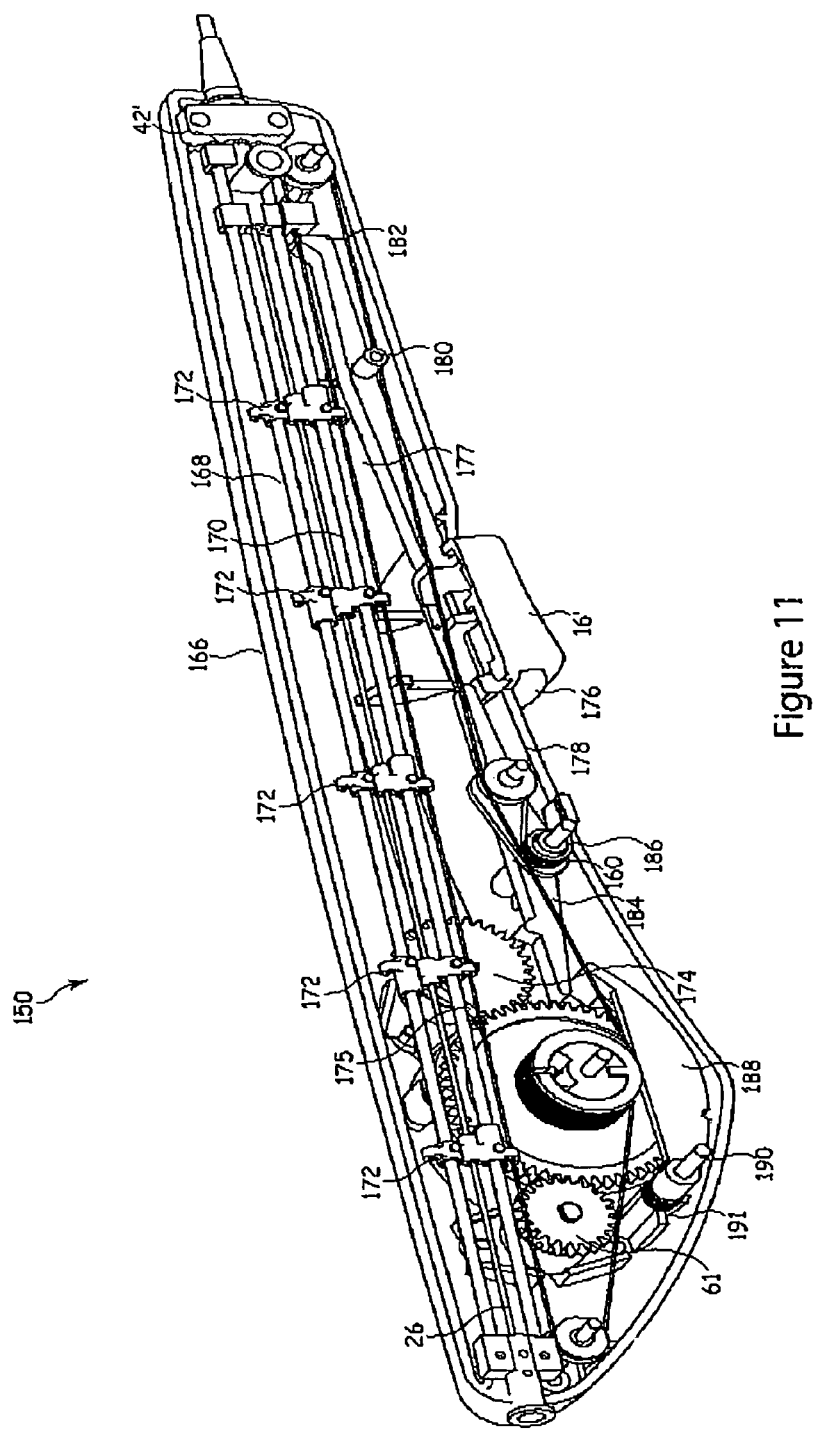
FIG. 11 is a perspective view of a handle assembly including the mechanism of FIGS. 10*a* to 10*c*, the handle assembly being shown with only one of its two casing halves.

Referring now to FIGS. 10*a* to 10*c*, there is shown another embodiment of a withdrawal mechanism for the handle assembly. The primary components of the assembly 150 are the same as the other embodiments described above and thus only those components which interact with the elements specific to this embodiment are shown in FIGS. 10A to 10C. FIG. 11, which is discussed below, shows the other components of the system of this embodiment.

The toothed wheel 50, at the rear of which the spiral spring 90 is visible, is provided with a spool 48', which in this embodiment is larger in diameter than the spool 48 of the above-described embodiments but is not necessarily so. The spool 48' is provided with a slot 49' extending at least partway longitudinally along its outer surface, leading to an enlarged recess 51' within the spool 48'. As can be seen in particular with regard to FIGS. 10*a* and 10*c*, the recess 51' is able to accommodate two beads 152 of a draw cable 154. The slot 49' is sufficiently narrow to prevent the passage of the beads 152 therethrough, such that the beads are tied in the spool 48' once the handle is assembled.

The outer circumferential surface of the spool 48' is threaded.

The draw cable 154, which may be made of a metal, nylon or any other suitable material, is arranged in a loop in the handle assembly with its two ends held by their beads 152 to the spool 48', as will be apparent in particular from FIG. 10*c*. A rearmost end 153 of the draw cable 154 wraps around the pulley wheel 46 at the proximal (rear) end of the handle assembly and is able to slide therearound. A front most end 155 of the draw cable 154 wraps around a second pulley wheel 146 at the distal (front) end of the handle assembly. The ends 156 of the draw cable 154 are wrapped in opposing directions for a few turns each around the spool 48', as will be apparent in particular in FIG. 10*c*. The turns of the cable 154 fit within the grooves of the threaded outer surface of the spool 48'. They are wrapped in such a way that when the toothed wheel 50 rotates (to thereby rotate the spool 48'), one of the ends 156 of the draw cable 154 wraps further along the channel or threading in the outer surface of the spool 48' while the other end 156 unwraps by an equivalent amount. The channel formed by the threaded outer surface of the spool 48' ensures that the cable windings around the spool 48' are kept separate from one another as they wrap and unwrap around the spool 48'. When the toothed wheel is rotated in the opposite direction, the order of wrapping and unwrapping is reversed. Thus, the effective length of the draw cable 154 remains the same as the spool 48' rotates. Systems of this nature are known in other applications.

Adjacent the distal end 155 of the draw cable there is provided, fixed to the cable, another bead 157. The arrangement is such that when the toothed wheel 50 is made to rotate by the unwinding of the spring 90, i.e., upon actuation of the trigger 16, the bead 157 is moved in a proximal (rearward) direction by the rotation of the spool 48'.

As will be seen particularly in connection with FIGS. 10a and 10b, the bead 157 sits within a slotted cup 159 in a clip 42'. As a result, movement of the bead 157 in a proximal (backward) direction pulls the clip 42' proximally and thus likewise pulls the body element 20 of the introducer. This in turn pulls the sheath 14 backwards to allow release of a stent carried on the introducer.

The advantage of the draw cable 154 is that this can prevent the occurrence of slack in the draw elements, as might occur in some instances with a single sided draw ribbon or string of the type shown in FIGS. 3 to 8, for example. The latter can become loose if, for instance, the body portion 20 of the introducer is pushed back during handling before actuation of the trigger 16.

In order to keep the draw cable 154 under constant tension, there is preferably provided a tensioning member 160. This is in the form of a finger pivoted at one end 164 to a suitable pivot element (not shown) provided in the casing, for example, and which has at is other end a guide wheel 162. The finger 160 is preferably constantly biased upwards (as viewed in the drawings), and in a direction to press onto the draw cable 154, by a spring element (not shown). As it does so, the finger 160 keeps the draw cable 154 under constant tension.

It is envisaged in some embodiments that the finger 160 could also act as a speed control element, for example by a suitable coupling to the trigger 16 so as to press to a greater or lesser extent against the draw cable 154. A greater pressing force will tend to apply greater friction to the draw cable 154 and thus slow its movement.

In other embodiments, speed control devices similar to those shown in FIGS. 6, 7a and 7b or 8, 9a and 9b could be used. If a speed control similar to that of FIGS. 8, 9a and 9b is used, this could also act as a tensioning device in place of the finger 160.

The mechanism of FIGS. 10A to 10C is shown located within a casing half 166 in FIG. 11, in which the trigger 16' is in an extended, non-use, position. The casing 166 includes a number of protrusions, slots, recesses and the like to accommodate and hold the various components of the assembly as well as the guide wire cannula 26 and two support rods or cannulae 168, 170. The support rods 168, 170 ensure that the mechanism remains straight during operation of the handle assembly. Located slidingly on the support rods 168, 170 and on the guide wire cannula 26 are a plurality of sliders 42' and 172. These are spaced at regular intervals along the support rods 168, 170 and cannula 26 and serve to ensure that these components remain parallel as the spring mechanism operates and as this pulls back the outer sheath of the catheter assembly. The sliders 42' and 172 are pushed backwards (that is to the rear end of the handle assembly 150) as the outer sheath is withdrawn, until they form a stack at the end of the handle 150.

It is envisaged that there may be provided a mechanism for ensuring that the sliders 172 do not move unintentionally before operation of the handle in a clinical procedure, for example during transportation and handling. A suitable mechanism involves tying the sliders 172 to one another by a thread or string, such that they are restricted from increasing their spacing relative to one another but can still be pushed together. It will be apparent that such a thread would be tied to the front slider 46' and to the casing at the rear end of the handle 150, and in between to the sliders 172 in a series coupling. Other mechanisms providing a similar function could also be used.

The embodiment of FIG. 11 also shows the provision of a two-speed damper element 174. This element 174 is structurally the same component as the damper 61 with the exception of having its gear wheel modified. The gear wheel has a portion of missing teeth, conveniently achieved by way of a section of the gear wheel being in effect cut off by a straight "cut line" 175. As a result, while the teeth of the damper wheel 174 engage the toothed wheel 50, the damper 174 provides an additional dampening force in addition to that of the damper 61. Once the damper 174 has rotated around the wheel 50 sufficiently such that the portion thereof with missing teeth becomes aligned with the teeth of the toothed wheel 50, the damper 174 becomes disengaged from the wheel 50. When this occurs, the damper 174 no longer provides any dampening force on the wheel 50, as a result of which the wheel 50 can rotate under the lower restraining and dampening force generated by the single damper 61. This dampening arrangement thus applies a higher dampening force at the start of the operation of the handle, so as to pull back the sheath at a slower rate, and then a lower dampening force for the remainder of the action, thereby allowing a higher rate of withdrawal of the sheath.

The damper 174 is preferably sized (i.e., geared) such that it provides for a specified amount of retraction of the sheath at the first, lower speed, typically for the first phase of deployment of the medical device carried on the introducer. It will be appreciated that this amount or distance can be readily controlled by the gearing ratio of the damper 174 relative to the toothed wheel 50 and/or by the initial rotational position of the damper 174.

The embodiment of FIG. 11 also shows another version of trigger assembly. The trigger 16' includes an integral safety button 176 which will normally extend out of the trigger 16' so as to abut against the outer casing 178 of the assembly and thus to prevent the trigger 16' from being depressed. In this position it cannot be pressed inwardly, as shown in FIG. 11, until the safety button 176 has itself been pressed into the trigger body 16'. A suitable spring element biases the safety button or lock 176 towards its outward position.

Figure 17:
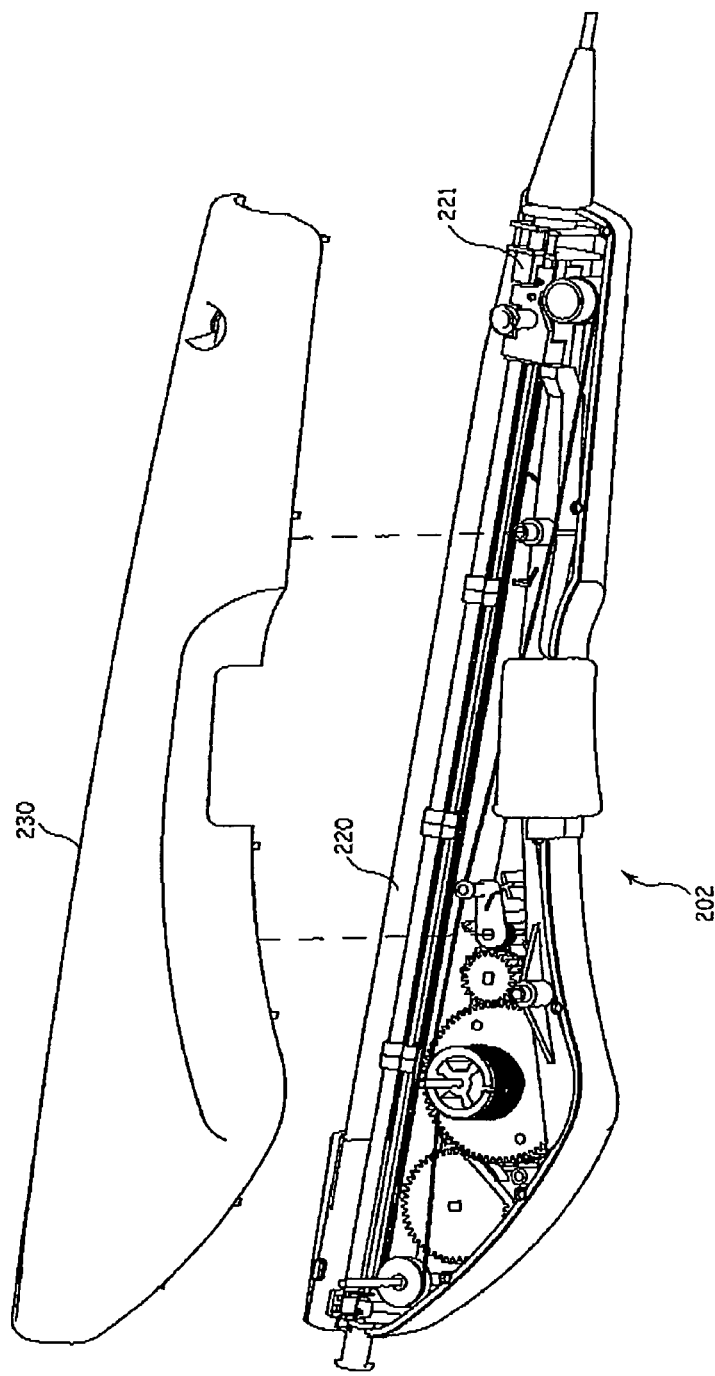
Figure 18:
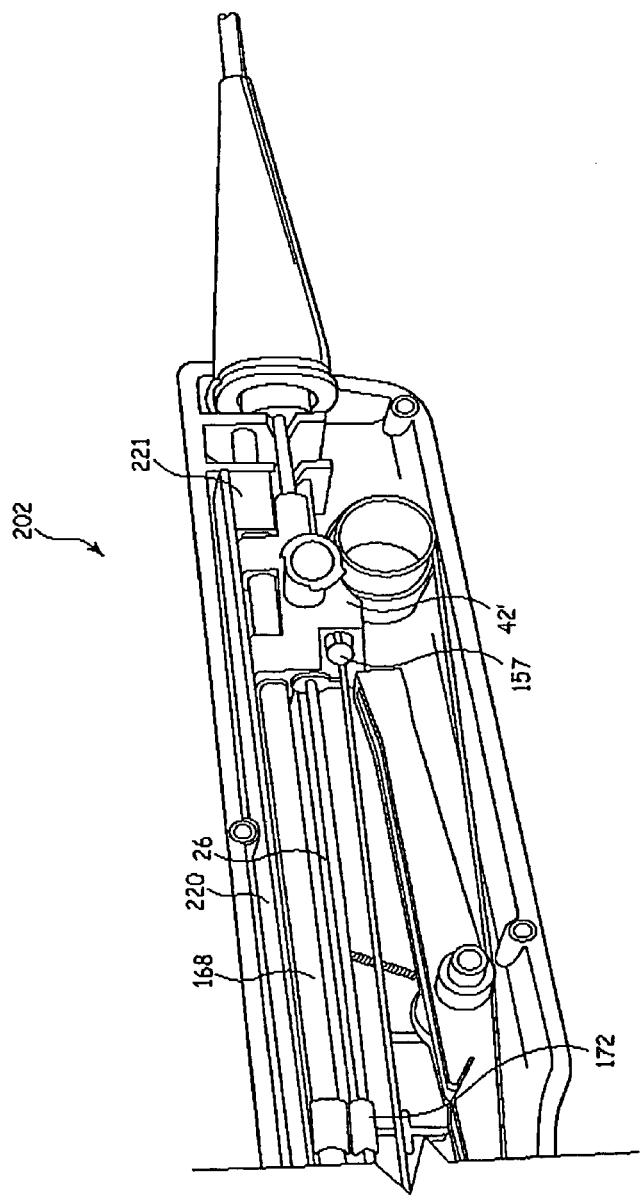

The trigger 16' includes an arm 177 which pivots about a pivot 180. The trigger button is at one end of the arm 177 while the other end includes a shoulder 182 which, when the trigger is in its locking position, abuts against the slide element 46' to prevent this from being pulled in a proximal direction and into the casing 150. FIG. 17 shows an analogous embodiment of trigger assembly with the shoulder in a blocking position.

The trigger assembly also includes a yoke 184 which is pivotable about a pivot pin 186 (in the embodiment shown the pivot pin 186 also supports the tensioning member 160). The yoke 184 includes one end which sits on the trigger 16' and another which cooperates with a locking element 188. The locking element 188 is pivotably attached to a pin 190 and is biased, by a suitable spring 191 for example, towards the toothed wheel 50. The locking element 188 includes at least one toothed or shouldered member which is able to engage the toothed wheel 50 such that when it is in an upper position, as viewed in FIG. 11, it locks the wheel 50 from rotation.

When the trigger 16' is depressed the yoke 186 is pivoted counter-clockwise to push the free end of the locking element 188 out of the way of the toothed wheel 50 and thereby allow the latter to rotate. If the trigger 16' is released, it will return to its lower or outer position (by means of a suitable sprung element, not shown), thereby allowing re-engagement of the locking element 188 to the wheel 50.

Referring now to FIGS. 12 to 18, there is shown another embodiment of handle assembly 202 in various stages of its construction. The assembly 202 comprises the same general components as the embodiment of FIGS. 10 and 11 and only the principal differences are thus described below.

The two speed damper element 204, fitted in this embodiment at the back end of the handle 204 (seen also in FIG. 13), includes a flexible arm 206 which extends from one end of the toothless zone 210 and circumscribes an arc substantially the same as the radius of the base of the teeth 208. The flexible arm 206 reduces or prevents the damper 204 from jumping when the last tooth 208 by the cut-out section 210 reaches the toothed wheel 50.

Figure 14:
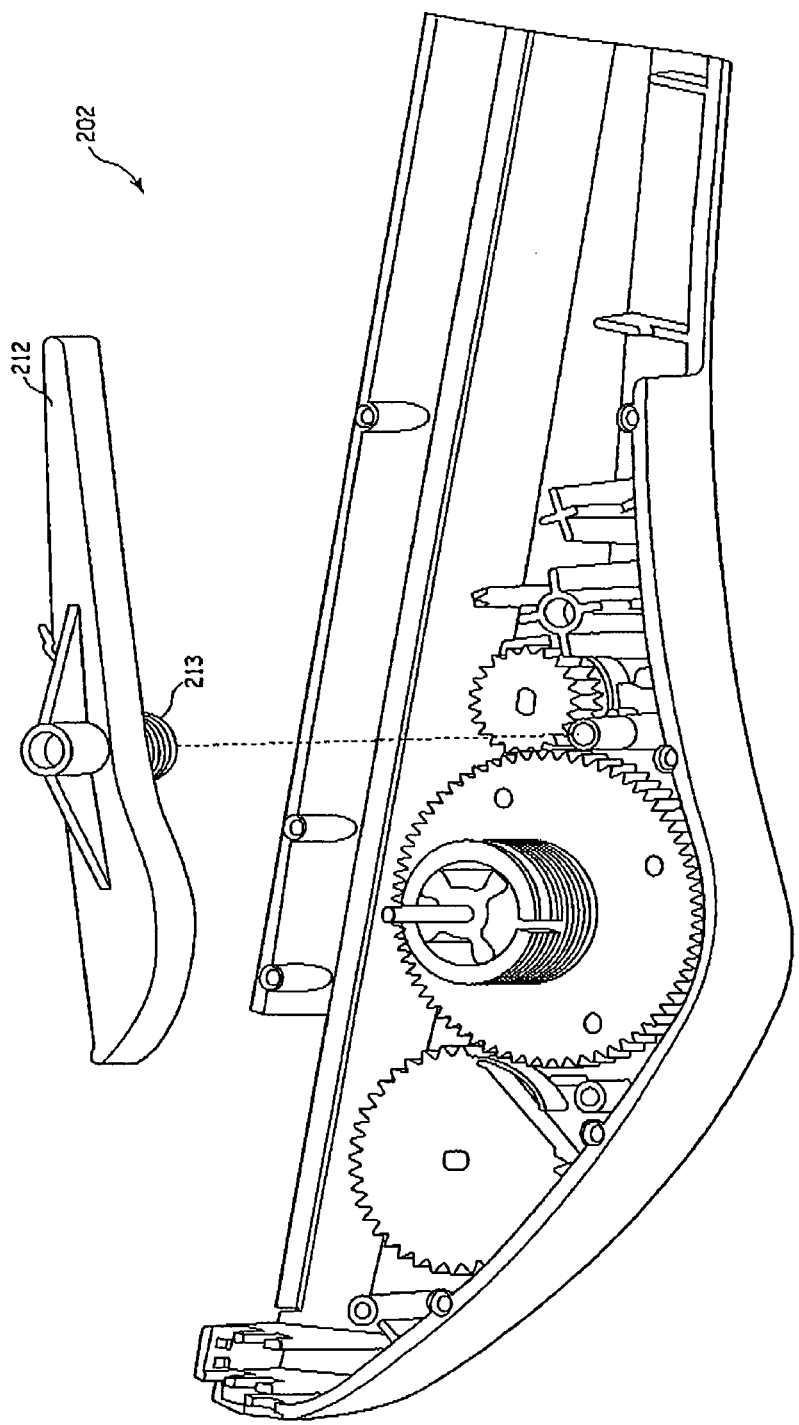
Figure 15:
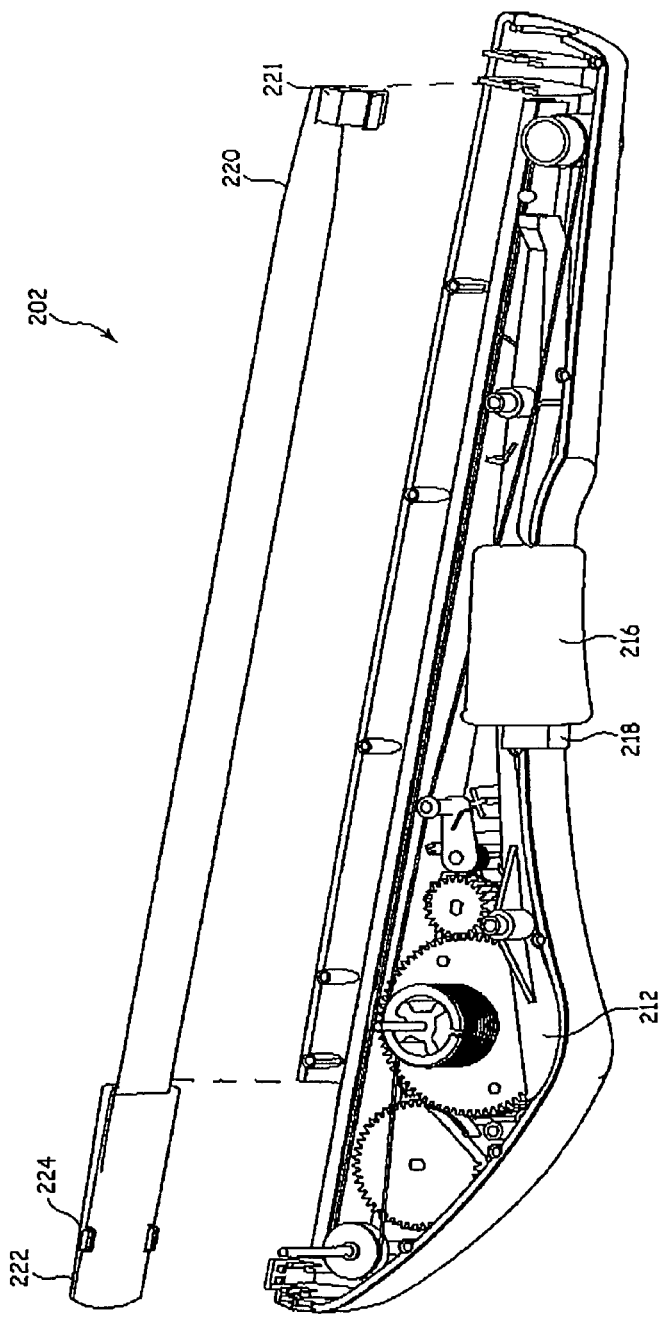

FIGS. 14 and 15 show the provision of a combined yoke and locking element 212 which is normally biased (for example by means of torsion spring 213) against the toothed wheel 50. FIG. 15 shows the trigger 216 and safety button 218 in the locked position.

Figure 16:
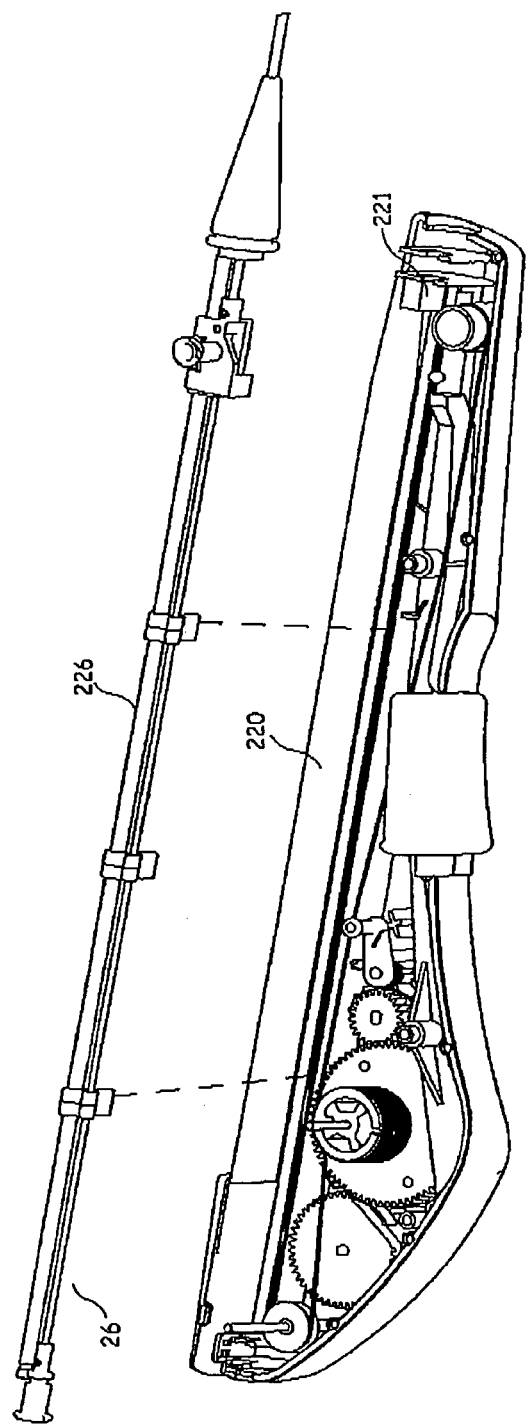

FIG. 16 shows a single guide rod which in this embodiment is held to the casing at appropriate support locations.

Referring now to FIG. 17, it can be seen that the other half 230 of the casing is substantially identical to the first half, although it will be provided with protrusions and recesses appropriate to support and locate those parts of the components to which is it adjacent and with which it interacts once assembled.

Also shown in FIGS. 15 to 18 is a rapid deployment tab or strip 220 which fits into an elongate space formed by the two handle halves and which runs just underneath the top of the handle 202 when its two halves are assembled together. The elongate space extends from the distal end to the proximal end of the handle. The rapid deployment strip 220 thus extends and covers the entirety of the top zone of the sheath withdrawal mechanism. The rapid deployment strip 220 includes a pull element 222 at the proximal end of the handle 202 and is usually locked thereto by side tabs 224. At the distal end of the strip 220 there is provided an anchor element 221 which, as can be seen clearly in FIGS. 17 and 18, fits distally of the clip 42' of the retraction mechanism. The anchor 221 is provided with a channel or slot for receiving the draw cable 154.

The pull element 222 can be grasped by a physician, for example with a nail or finger tip, to pull it away from the casing 202 of the handle, thereby allowing it to be grasped properly by the physician. This can then be pulled in a proximal direction so as to pull the strip 220 out of the handle form the proximal end of the handle. In so doing, the anchor 221 is also pulled back, thus pulling back the clip 42' and effecting manual retraction of the sheath. This can be useful in cases where the surgeon, for a particular medical reason for instance, needs to effect deployment in an emergency and can thus override the automatic operation of the handle.

The embodiments of FIGS. 11 to 18 show a two speed handle assembly, which will be advantageous in many applications. It is envisaged that there could be provided two or more speed control damper elements to give the handle three or more distinct working speeds. Of course, a two or multi-speed handle assembly could also incorporate a variable speed control device of the type disclosed herein and shown, for example, in FIGS. 6 to 8. Similarly, the safety override function facilitated by the removable cover strip 220 could be incorporated into any of the other embodiments described herein.

Figure 19:
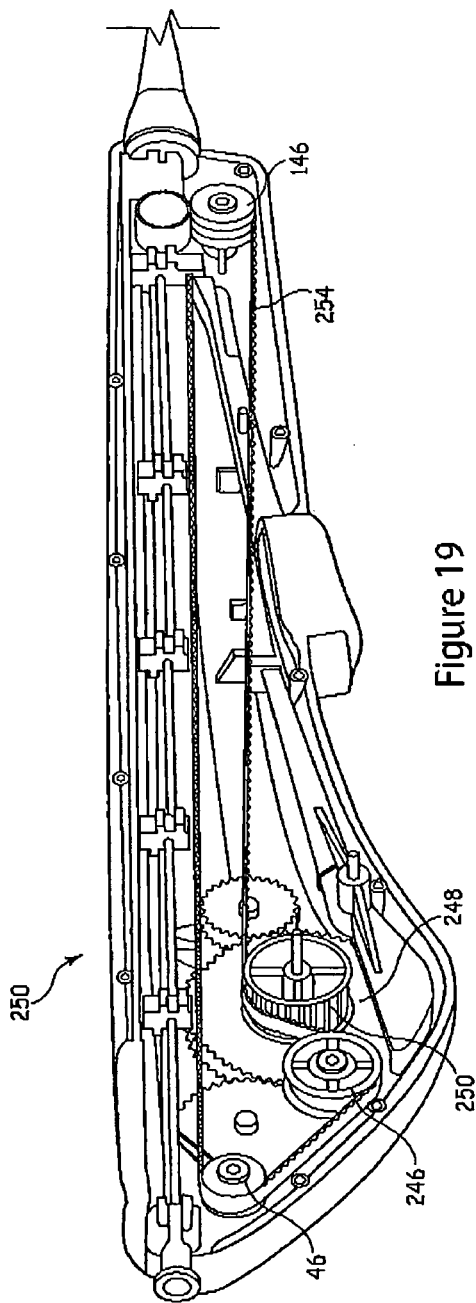
FIGS. 19 and 20 are elevational views of the internal components of another embodiment of handle assembly.
Figure 20:
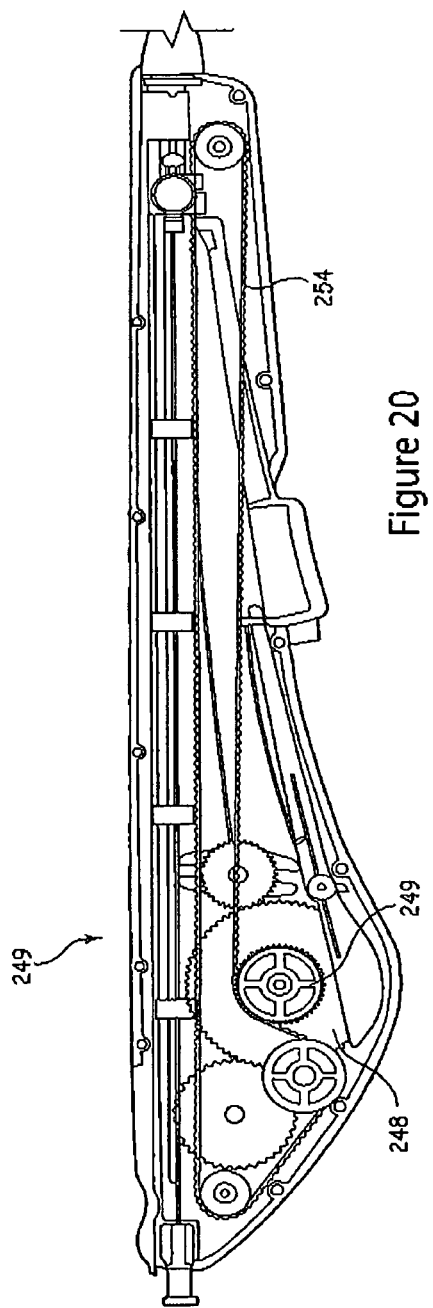

Referring now to FIGS. 19 to 20, there is shown another example of handle assembly 250 in accordance with the invention. The majority of the components of the assembly 250 are the same as or similar to those of the embodiments described above. The primary difference with this assembly is that in place of a pull strip or cable there is provided an endless toothed belt 254 which is held around pulley wheels 46, 146, 246 and engages a toothed spindle 249 of the toothed wheel 248. As the toothed wheel 248 rotates, it will cause the toothed belt 254 to which it is engaged to be pulled, thereby causing retraction of the sheath in the manner described above. The toothed belt could be slightly resilient, allowing it to take up any slack in the mechanism and ensuring good contact and engagement with the spindle 249 of the toothed wheel 248.

Figure 21:
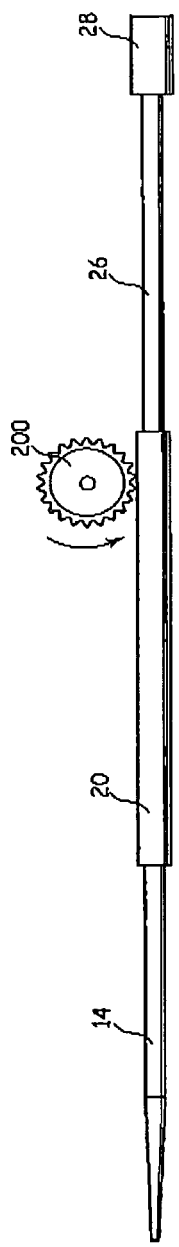
FIG. 21 is a side elevational view in schematic form of another embodiment of deployment device.

Other embodiments of deployment device are shown in FIGS. 21 to 25. Referring first to FIG. 21, there is shown in schematic form a handle arrangement 200 with a toothed wheel which engages the outer surface of the body member 20 of the introducer in order to pull this in a distal direction and thereby in order to pull back the outer sheath 14. A mechanism is provided for holding the hub 28, which can be similar to that of the embodiments described above. The toothed wheel may simply have teeth sharp enough to dig in to the material of the body member 20 or may cooperate with a toothed runner provided in or on the body member 20.

FIGS. 22 to 24 show another embodiment which is provided with a very simple housing 300 which holds the spiral spring 90 and toothed wheel 50 arrangement, and which also holds the hub 28 by a suitable grasping member 302. The strap 44 is provided with its own grasping member 304 which fits onto and grasps the body member 20 of the introducer. A simple trigger mechanism 306, having similarities to the trigger 16 of the embodiment of FIGS. 1 to 9B, unlocks the toothed wheel 50 for rotation by the spring 90, which thus pulls the strap 44 into the housing 300, to be wound onto the spool 308. This is a very simple handle mechanism which may be useful in certain circumstances. In particular, it can be connected by simply snap fitting the connectors 302 and 304 to an existing introducer. The principles of operation of the embodiments shown in FIGS. 22 to 24 are similar to those of the embodiments described above.

Figure 25:
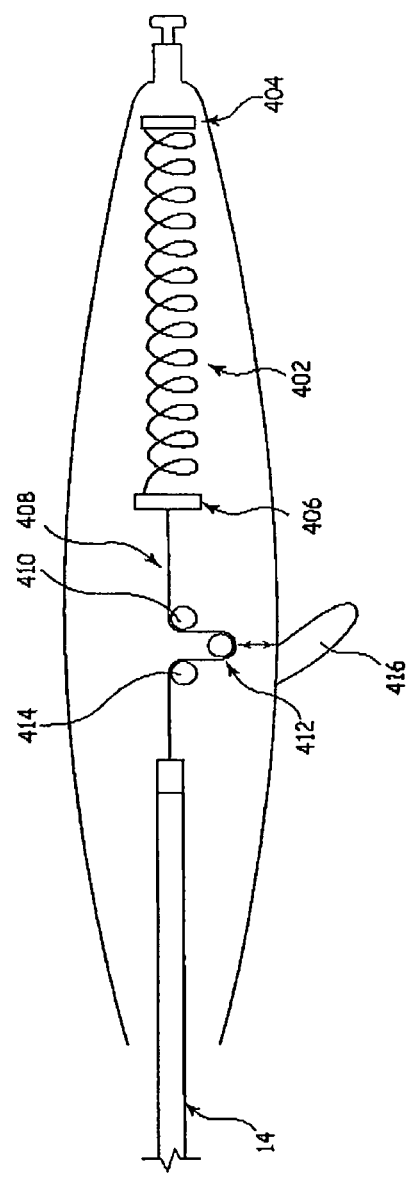
FIG. 25 is a side elevational view in schematic form of another embodiment of sprung loaded retraction handle assembly.

Referring to FIG. 25, there is shown in schematic form another embodiment of sprung loaded handle assembly 400. Only the principal components of the device are shown in the Figure for the sake of clarity.

This embodiment uses a coil spring 402 arranged substantially aligned with the longitudinal axis of the handle 400 and thus of the direction of retraction within the handle assembly. A proximal end of the spring 402 is attached at a suitable attachment point 404. The other is coupled to a movable connection member 406. The connection member is attached to a ribbon or strap 408, similar to the ribbon 44 of the embodiments of FIGS. 1 to 9B. An arrangement of bosses 410, 412, 414, equivalent to the arrangement of FIGS. 8 to 9b, provides a labyrinthine path for the strap 408, the boss 412 being movable upwardly and downwardly by the trigger 416 to provide a variable resistance to the movement of the strap 408 and thus speed control to the retraction of the spring 402 and consequential retraction of the sheath 14. The trigger 416 also includes a lock element (not shown) to lock the device so as to prevent retraction until the trigger is actuated. A suitable lock element will be apparent to one skilled in the art given the disclosures herein and is therefore not described in detail herein.

The spring 402 is provided in the handle 400 in a stretched condition, such that it provides a biasing force on the member 406 to the right in the view of the drawing. Depression of the trigger 416 releases the spring 402 from its locked condition and allows movement of the movable connection member 406 to thereby pull back the ribbon 408 and the sheath 14. The labyrinthine path through the bosses 410-414, the degree of which is controlled by the amount of depression of the trigger 416, controls the speed of the retraction of the sheath 14, in similar manner to the equivalent system of FIGS. 8 to 9B. Thus, the device can provide for controlled retraction of the sheath 14.

It will be appreciated that the spring 402 will generally provide a varying restoring force and thus a varying force of retraction of the sheath 14. In some applications this is not material or even advantageous, such as applications where it is not desired to retract the sheath 14 by a large amount or where it is desired to have the retraction force drop substantially, such as when the friction between the sheath and the inner catheter drops rapidly after the start of retraction.

It is envisaged that the coil spring 402 could be made of a shape memory material, allowing this to generate a varying retraction force as this is heated to above its transition temperature. A combination of springs 402 is also envisaged.

It is to be understood that the features and elements of the various embodiments described above could be incorporated into the other embodiments disclosed herein and contemplated by the teachings of the present patent application.

What is claimed is:

1. A deployment assembly for deploying one or more components of an endovascular introducer assembly provided with a retractable element, the deployment assembly comprising an external manipulation element having a locked and unlocked state, and an actuator element coupled to the external manipulation element, said actuator element comprising a spiral spring that is initially biased and restrained by the external manipulation element in said locked state from exerting a restoring force, wherein said spring is released by actuation of said external manipulation element to said unlocked state, said spring thereby exerting said restoring force on a wheel to retract said retractable element in response to said external manipulation element being actuated from said locked state to said unlocked state, and further comprising a first damper and a second damper, said first and second dampers being rotary dampers coupled to said wheel, said second damper being a two-speed damper that disengages from said wheel after a first phase of retraction of the retractable element, said first and second dampers applying a higher dampening force on said wheel to retract said retractable element at a slower rate during said first phase of retraction, and said first damper applying a lower dampening force on said wheel than said first and second dampers to retract said retractable element at a higher rate after said first phase.

2. A deployment assembly according to claim 1, comprising a speed control device operable to control the speed of operation of the actuator element.

3. A deployment assembly according to claim 2, wherein the speed control device provides for adjustable speed of retraction.

4. A deployment assembly according to claim 3, wherein the speed control device is separately actuatable relative to the actuator element.

5. A deployment assembly according to claim 4, wherein the speed control device is a part of the actuator element.

6. A deployment assembly according to claim 1, comprising a discrete speed control device operable to control the speed of retraction at least two different speeds.

7. A deployment assembly according to claim 1, wherein the assembly includes a handle element carrying the actuator element.

8. A deployment assembly according to claim 7, wherein the handle element is designed to fit to an external manipulation end of an introducer.

9. A deployment assembly according to claim 1, comprising a trigger device for triggering the actuator element to retract said retractable element attached thereto.

10. A deployment assembly according to claim 9, wherein the trigger device includes a stop device operable to stop operation of the actuator element.

11. A deployment assembly according to claim 1, wherein said second damper comprises teeth engaged with teeth of said wheel and a portion of missing teeth, said missing teeth disengaging with said teeth of said wheel to disengage said second damper.

12. A deployment assembly according to claim 11, wherein said second damper further comprises a flexible arm circumscribing an arc along said missing teeth.

13. A deployment assembly for deploying one or more components of an endovascular introducer assembly provided with a retractable element, the deployment assembly comprising an external manipulation element having a locked and unlocked state, an actuator element, a coupling element for coupling the actuator element to said retractable element and a speed control device for controlling the speed of operation of the actuator element, said actuator element comprising a spiral spring that is initially biased and restrained by the external manipulation element in said locked state from exerting a restoring force, wherein said spring is released by actuation of said external manipulation element to said unlocked state, said spring thereby exerting said restoring force on a wheel to retract said retractable element in response to said external manipulation element being actuated from said locked state to said unlocked state, and further comprising a first damper and a second damper, said first and second dampers being rotary dampers coupled to said wheel, said second damper being a two-speed damper that disengages from said wheel after a first phase of retraction of the retractable element, said first and second dampers applying a higher dampening force on said wheel to retract said retractable element at a slower rate during said first phase of retraction, and said first damper applying a lower dampening force on said wheel than said first and second dampers to retract said retractable element at a higher rate after said first phase.

14. A deployment assembly according to claim 13, wherein the speed control device provides for adjustable speed of retraction.

15. A deployment assembly according to claim 14, wherein the speed control device is separately actuatable relative to the actuator element.

16. A deployment assembly according to claim 15, wherein the speed control device is a part of the actuator element.

17. A deployment assembly according to claim 13, comprising a discrete speed control device operable to control the speed of retraction at least two different speeds.

18. A deployment assembly according to claim 13, wherein the assembly includes a handle element carrying the actuator element.

19. A deployment assembly according to claim 18, wherein the handle element is designed to fit to an external manipulation end of an introducer.

20. A deployment assembly according to claim 13, comprising a trigger device for triggering the actuator element to retract said retractable element attached thereto.

21. A deployment assembly according to claim 20, wherein the trigger device comprises a stop device operable to stop operation of the actuator element.

22. A deployment assembly according to claim 13, wherein the coupling element comprises an elongate flexible member attachable to said retractable element to couple said retractable element to the actuator element.

23. A deployment assembly according to claim 22, wherein the elongate flexible member is a cable, cord, strip or band of flexible material.

24. A deployment assembly according to claim 23, wherein the speed control device is operable to control a frictional force applied to the elongate flexible member.

25. A deployment assembly according to claim 24, wherein the speed control device includes an adjustable labyrinthine path for the elongate flexible member.

26. A deployment assembly according to claim 25, wherein said labyrinthine path is provided with a plurality of projecting surfaces projecting into the path of the elongate flexible member.

27. A deployment assembly according to claim 26, wherein one or more of the projecting surfaces is movable to adjust sliding friction applied to the elongate flexible member.

28. A deployment assembly according to claim 25, wherein said second damper comprises teeth engaged with teeth of said wheel and a portion of missing teeth, said missing teeth disengaging with said teeth of said wheel to disengage said second damper.

29. A deployment assembly according to claim 22, including a spindle upon which the elongate flexible member can be made to wind on retraction of the retractable element.

\* \* \* \* \*